(12) United States Patent
Kuga

(10) Patent No.: US 12,711,693 B2
(45) Date of Patent: Aug. 18, 2026

(54) ULTRASONIC IMAGE PROCESSING APPARATUS, ULTRASONIC DIAGNOSTIC APPARATUS, AND ULTRASONIC IMAGE PROCESSING METHOD

(71) Applicant: CANON KABUSHIKI KAISHA, Tokyo (JP)

(72) Inventor: Itsuki Kuga, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 146 days.

(21) Appl. No.: 18/431,092

(22) Filed: Feb. 2, 2024

(65) Prior Publication Data

US 2024/0265622 A1 Aug. 8, 2024

(30) Foreign Application Priority Data

Feb. 3, 2023 (JP) ................................ 2023- 015444

(51) Int. Cl.
*A61B 8/06* (2006.01)
*A61B 8/00* (2006.01)
*G06T 15/08* (2011.01)

(52) U.S. Cl.
CPC .............. *G06T 15/08* (2013.01); *A61B 8/466* (2013.01); *A61B 8/483* (2013.01); *A61B 8/488* (2013.01); *A61B 8/5223* (2013.01); *G06T 2200/24* (2013.01); *G06T 2210/41* (2013.01); *G06T 2210/62* (2013.01)

(58) Field of Classification Search
CPC . G06T 15/08; G06T 2200/24; G06T 2210/41; G06T 2210/62; A61B 8/466; A61B 8/483; A61B 8/488; A61B 8/5223; A61V 8/06
See application file for complete search history.

(56) References Cited

U.S. PATENT DOCUMENTS

| | | | | |
|---|---|---|---|---|
| 7,990,378 | B2 * | 8/2011 | Rabben | G06T 15/08 345/419 |
| 10,182,793 | B2 * | 1/2019 | Satoh | A61B 8/523 |
| 11,304,677 | B2 * | 4/2022 | Du | A61B 8/469 |
| 2014/0187948 | A1 * | 7/2014 | Gerard | A61B 8/469 600/443 |
| 2014/0330121 | A1 * | 11/2014 | Kim | A61B 8/485 600/438 |
| 2017/0119356 | A1 * | 5/2017 | Steininger | A61B 8/488 |
| 2022/0257218 | A1 * | 8/2022 | Zhang | A61B 8/54 |

FOREIGN PATENT DOCUMENTS

| | | |
|---|---|---|
| JP | 2001-17428 A | 1/2001 |

* cited by examiner

*Primary Examiner* — Xiao M Wu
*Assistant Examiner* — George Renze
(74) *Attorney, Agent, or Firm* — Oblon, McClelland, Maier & Neustadt, L.L.P.

(57) ABSTRACT

According to one embodiment, an ultrasonic image processing apparatus includes processing circuitry. The processing circuitry is configured to acquire volume data based on ultrasonic signals collected by 3D color doppler mode, wherein each voxel value of the volume data includes at least a value of velocity of fluid and a value of power representing intensity of echo signals of the fluid. The processing circuitry is configured to generate a velocity rendering image by volume rendering the volume data using an opacity map in which a relationship between the opacity of the voxel and both the velocity and the power is defined.

13 Claims, 13 Drawing Sheets

ULTRASONIC IMAGE PROCESSING APPARATUS, ULTRASONIC DIAGNOSTIC APPARATUS, AND ULTRASONIC IMAGE PROCESSING METHOD

CROSS-REFERENCE TO RELATED APPLICATIONS

This application claims the benefit of priority of Japanese Patent Application No. 2023-015444, filed Feb. 3, 2023, the entire contents of which are incorporated herein by reference.

FIELD

Embodiments described herein relate generally to an ultrasonic image processing apparatus, an ultrasonic diagnostic apparatus, and an ultrasonic image processing method.

BACKGROUND

The ultrasonic diagnostic apparatus radiates ultrasonic pulses or continuous ultrasonic waves generated by a vibrating element built into the ultrasonic probe into the object, converts ultrasonic reflections caused by differences in the acoustic impedance of the object tissue into electrical signals using the vibrating element, and collects information inside the object noninvasively. Medical examinations using ultrasonic diagnostic apparatus can easily generate and collect medical images, such as tomographic images and three-dimensional images of the inside of an object, by touching the ultrasonic probe to the body surface. This allows for easy generation and collection of medical images such as tomographic images and three-dimensional images of the inside of an object by bringing the probe into contact with the body surface.

The imaging modes of ultrasonic diagnostic apparatus include B-mode, Doppler mode, and color Doppler mode. Among these imaging modes, the color Doppler mode can obtain information such as the velocity, dispersion, and power of the object's blood flow.

In the 3D color Doppler mode, which performs three-dimensional beam scanning, the values of the above parameters of velocity, dispersion, and power are acquired for each voxel of the volume data. When displaying velocity based on the acquired volume data, a velocity rendering image is generated by volume rendering the velocity volume data in which the voxel values are represented by the velocity values.

In general, volume rendering uses opacity curves that define opacity according to voxel values. In conventional volume rendering to generate a velocity rendering image from velocity volume data, an opacity curve for velocity is used.

In the conventional opacity curve for velocity, the "threshold" that defines the lower limit of the velocity displayed after volume rendering and the "transparency" used in the volume rendering process (or the opposite, the "non-transparency") are adjustable through the user interface.

However, the conventional volume rendering process for generating a velocity rendering image and the conventional opacity curve for velocity do not always produce the velocity rendering image desired by the user, and further improvement is required.

DETAILED DESCRIPTION

Hereinbelow, a description will be given of an ultrasonic image processing apparatus, an ultrasonic diagnostic apparatus, and an ultrasonic image processing method according to embodiments of the present invention with reference to the drawings.

According to one embodiment, an ultrasonic image processing apparatus includes processing circuitry. The processing circuitry is configured to acquire volume data based on ultrasonic signals collected by 3D color doppler mode, wherein each voxel value of the volume data includes at least a value of velocity of fluid and a value of power representing intensity of echo signals of the fluid. The processing circuitry is configured to generate a velocity rendering image by volume rendering the volume data using an opacity map in which a relationship between the opacity of the voxel and both the velocity and the power is defined.

First Embodiment

Figure 1:
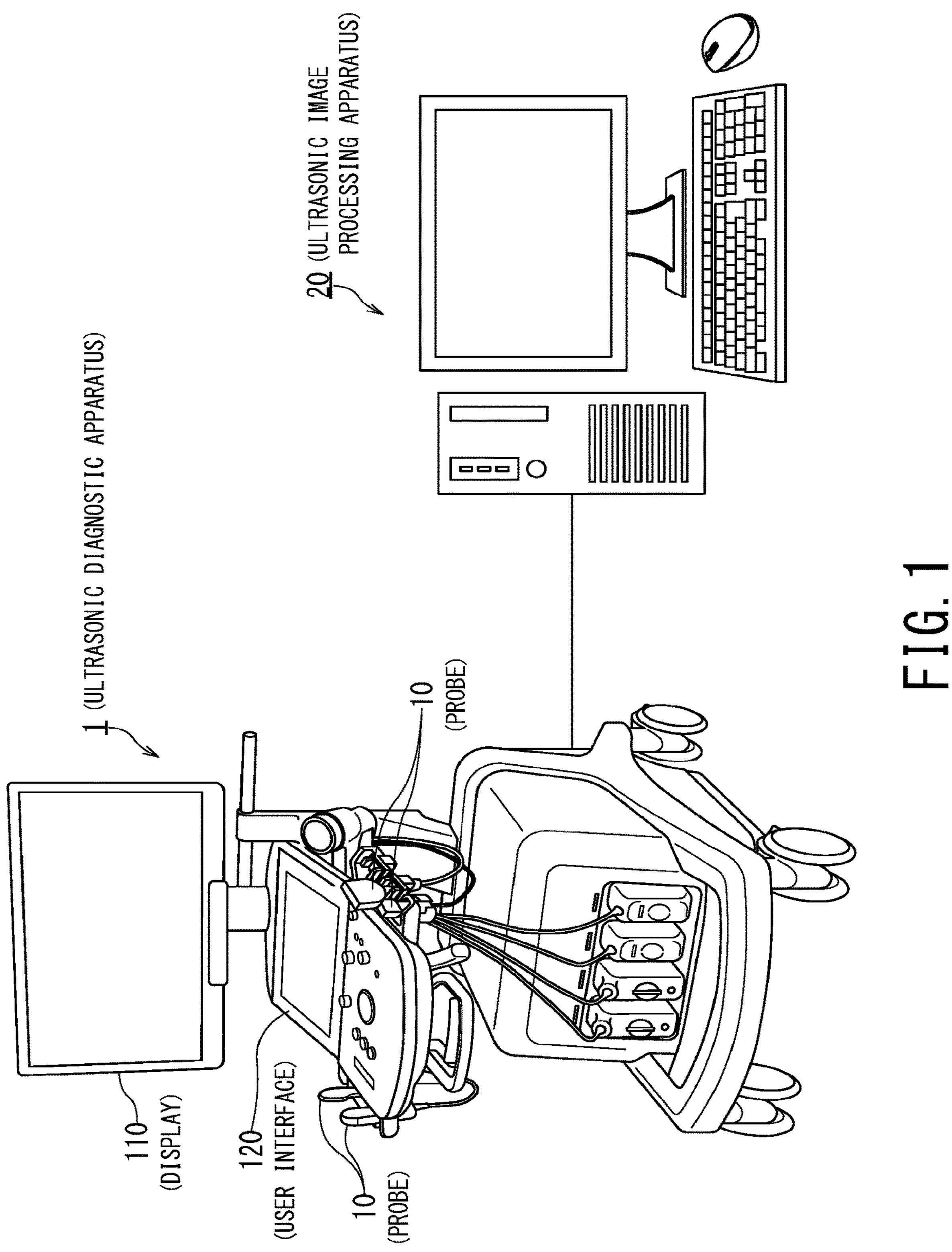
FIG. 1 is a perspective view showing an example of an appearance of an ultrasonic diagnostic apparatus and an ultrasonic image processing apparatus according to the first embodiment.

FIG. 1 is a perspective view showing an example of an appearance of an ultrasonic diagnostic apparatus and an ultrasonic image processing apparatus according to the first embodiment. As shown in FIG. 1, an ultrasonic diagnostic apparatus 1 has an apparatus body and a probe 10. The main body of the apparatus consists of the ultrasonic diagnostic apparatus 1 excluding the probe 10, and is provided with a display 110 and a user interface 120, in addition to various circuits (see FIG. 2) that are housed in a main body case with casters.

The display 110 displays ultrasound images and various data generated by various circuits of the device itself. The display 110 is composed of, for example, a liquid crystal display panel or an organic EL (Electro Luminescence) panel.

The user interface 120 is a device that allows the user to input various data and information into the device body or set various operation modes to the device body through user operation. The user interface 120 comprises, for example, a control panel 121 and a touch panel 122 (see FIG. 2).

The control panel 121, for example, is arranged with operation devices such as a trackball, various switches, dials, and the like, and by operating these operation devices, the user can input various data and information into the device body.

The touch panel 122 is a display and input device that includes a touch screen overlaid on a display panel such as an LCD panel. By touching or pressing the touch screen in accordance with the display on the display panel, various data and information can be input into the main unit of the device.

The ultrasonic image processing apparatus 20 is configured as a computer, such as a workstation or a personal computer, and is equipped with a display, a keyboard, a mouse, and a device body, as illustrated in FIG. 1. The specific configuration and functions of the ultrasonic image processing apparatus 20 are described below.

Figure 2:
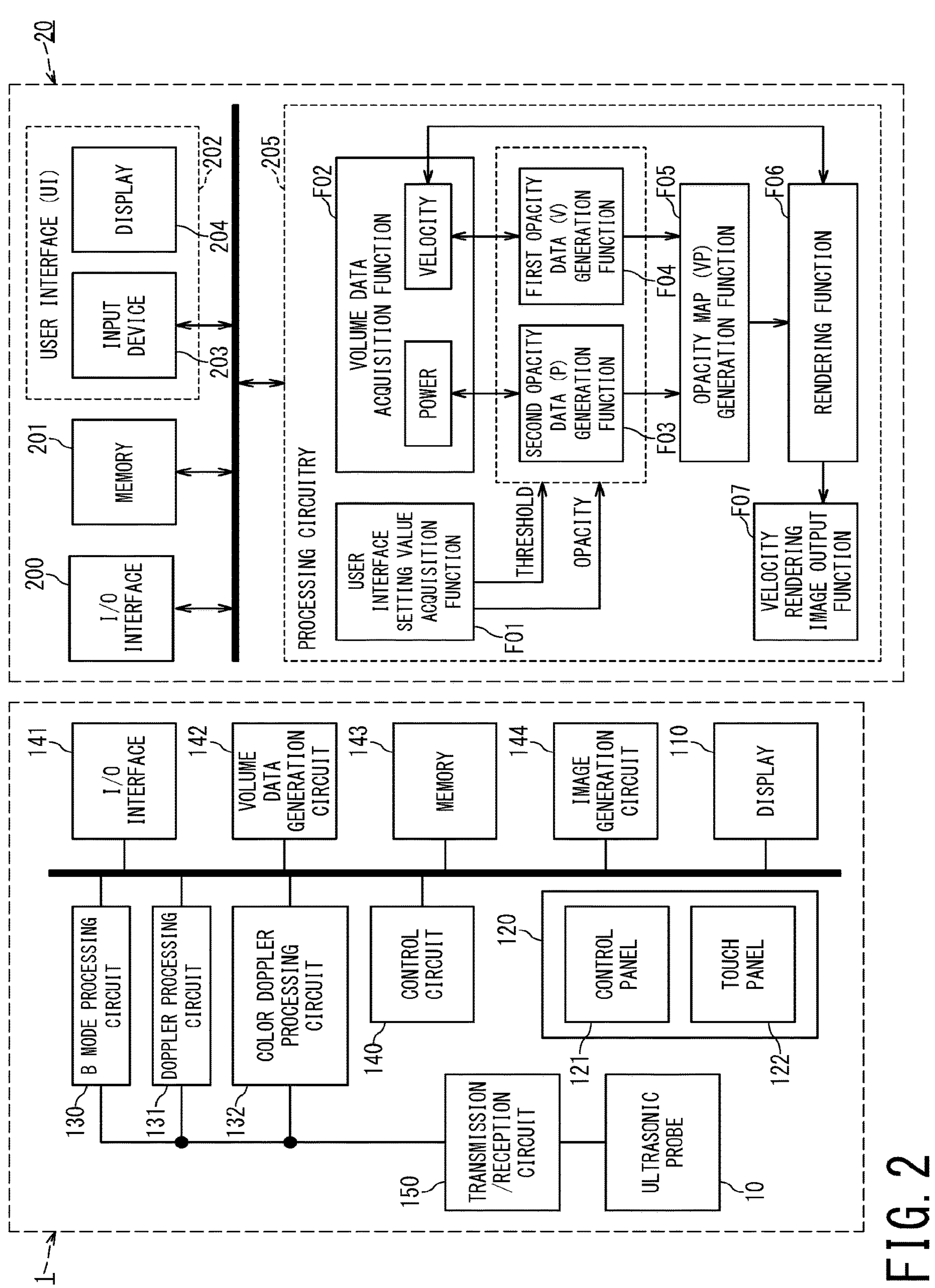
FIG. 2 is a block diagram showing an example of a configuration of the ultrasonic diagnostic apparatus and the ultrasonic image processing apparatus according to the first embodiment.

FIG. 2 is a block diagram showing an example configuration of the ultrasonic diagnostic apparatus 1 and the ultrasonic image processing apparatus 20 according to the first embodiment. Firstly, the ultrasonic diagnostic apparatus 1 will be described.

The ultrasonic diagnostic apparatus 1 is equipped with a probe 10, a transmission/reception circuit 150, and the user interface 120 with the control panel 121 and the touch panel 122 as described above. The ultrasonic diagnostic apparatus 1 also has a B-mode processing circuitry 130, a Doppler processing circuitry 131, a color Doppler processing circuitry 132, a control circuit 140, an I/O interface 141, a volume data generation circuit 142, a memory 143, an image generation circuit 144, and the display 110.

The probe 10 transmits ultrasonic signals into the object's body and receives echo signals reflected from the object's body. The probe 10 is provided with a number of ultrasonic transducers.

During transmission, the transmission/reception circuit 150 provides pulse signals to generate ultrasound pulses to each of the many ultrasound transducers of the probe 10. By setting the delay time for each of the ultrasonic transducers to a predetermined value, the transmission beam of the probe 10 is formed. During reception, the receive signals output from each ultrasonic transducer of the probe 10 are converted into digital signals, and then the weighted addition of the digitalized receive signals is used to form the receive beam. For example, the transmit and receive beams are scanned based on the scanning direction indicated by the control circuit 140.

The B-mode processing circuitry 130 performs processing on the received signals collected by the B-mode imaging method; in B-mode, the amplitude information (or intensity information) of the received signals is obtained by performing logarithmic detection processing, and the like, on the received signals collected while sequentially scanning the transmit and receive beams.

In the B mode of the ultrasonic diagnostic apparatus 1, two-dimensional scanning or three-dimensional scanning can be selected. When 3D scanning is selected, amplitude information is obtained for each voxel in 3D space corresponding to the scanning range.

The Doppler processing circuitry 131 processes the received signals collected by the Doppler mode imaging method. Doppler modes include continuous wave Doppler mode and pulsed Doppler mode. In continuous wave Doppler mode, the received signal is processed from the specified beam direction, and in pulsed Doppler mode, the received signal is processed from the specified beam direction and specified distance, and signal processing such as Fourier transform is performed to generate detailed data on blood flow velocity.

The color Doppler processing circuitry 132 performs processing on the received signals collected by the color Doppler mode imaging method. In the color Doppler mode, the received signals are collected by scanning the transmit and receive beams over a predetermined range in the azimuth direction in the case of two-dimensional scanning while transmitting and receiving multiple times in the same direction, or over a predetermined range in both the azimuth and elevation directions in the case of three-dimensional scanning. Then, for example, by performing autocorrelation processing on multiple received signals collected from the same direction, data (or indexes) related to blood flow (or body fluid flow) such as blood flow velocity, dispersion, and power can be obtained.

The velocity means the average velocity of the blood flow, which includes information about the direction of the blood flow. The average velocity of the blood flow may be expressed as a positive average velocity for blood flow flowing toward the probe 10 and a negative average velocity for blood flow flowing away from the probe 10. Dispersion is information indicating the dispersion of velocity (i.e., the variation of velocity). The power is information about the strength of the echo signal from the blood flow. These data are obtained for each pixel in the two-dimensional space corresponding to the scanning area in the case of two-dimensional scanning, and for each voxel in the three-dimensional space corresponding to the scanning area in the case of three-dimensional scanning.

The volume data generation circuit 142 generates three-dimensional volume data, which is an array of information or data obtained for each voxel in three-dimensional space when three-dimensional scanning is performed in B mode or color Doppler mode, corresponding to each voxel position.

The image generation circuit 144 converts the information or data collected in B mode, Doppler mode, and color Doppler mode into display images for display on the display 110, and also processes various auxiliary information to be added to the display images.

The display 110, as described above, is composed of, for example, an LCD panel or an organic EL panel, and displays the display image generated by the image generation circuit 144.

The memory 143 temporarily stores data and information generated by each of the above-mentioned circuits, and also stores programs necessary for software processing when each of the above-mentioned circuits is configured to perform software processing.

The I/O interface 141 is a wired or wireless communication interface circuit for exchanging various data and signals with external devices, such as an image server and the ultrasonic image processing apparatus 20 described below. The I/O interface 141 also includes communication interface circuits via the Internet or telephone lines, as well as read or write circuits for portable memory, for example, semiconductor memory such as USB memory, optical disks, magnetic disks, and the like.

Next, the ultrasonic image processing apparatus 20 will be described. The ultrasonic image processing apparatus 20 according to the embodiment is configured to perform volume rendering processing on the volume data generated by the ultrasonic diagnostic apparatus 1 in color Doppler mode.

The ultrasonic image processing apparatus 20 has an I/O interface 200, a memory 201, a user interface 202 with an input device 203 and a display 204, and processing circuitry 205.

The I/O interface 200, like the I/O interface 141 of the ultrasonic diagnostic apparatus 1, is used to transfer various data and signals to and from external devices, such as an image server and the ultrasonic diagnostic apparatus 1 described above. The I/O interface 200 is a wired or wireless communication interface circuit for exchanging various data and signals with external devices, for example, an image server or the ultrasonic diagnostic apparatus 1 described above. The I/O interface 200 may also include communication interface circuitry via the Internet or telephone lines, and may include read or write circuitry for portable memory, for example, semiconductor memory such as USB memory, optical disks, magnetic disks, etc.

The memory 201, for example, temporarily stores volume data acquired from the ultrasonic diagnostic apparatus 1, as well as various programs to be executed by the processing circuitry 205 described below.

The user interface 202 has the function of inputting and selecting various data and information to the ultrasonic image processing apparatus 20 by user operation using the input device 203, such as a mouse or keyboard, on the image displayed on the display 204.

The processing circuitry 205 is, for example, a circuit equipped with a CPU or a dedicated or general-purpose processor. The processor, for example, executes various programs stored in the memory 201 to perform a user interface setting value acquisition function F01, a volume data acquisition function F02, a second opacity data (P) generation function F03, a first opacity data (V) generation function F04, a capacity map (VP) generation function F05, a rendering function F06, and a velocity rendering image output function F07.

The processing circuitry 205 may be composed of hardware such as a field programmable gate array (FPGA) or an application specific integrated circuit (ASIC). These hardware can also realize the various functions described above. The processing circuitry 205 can also realize various functions by combining software processing with a processor and program and hardware processing.

Figure 3:
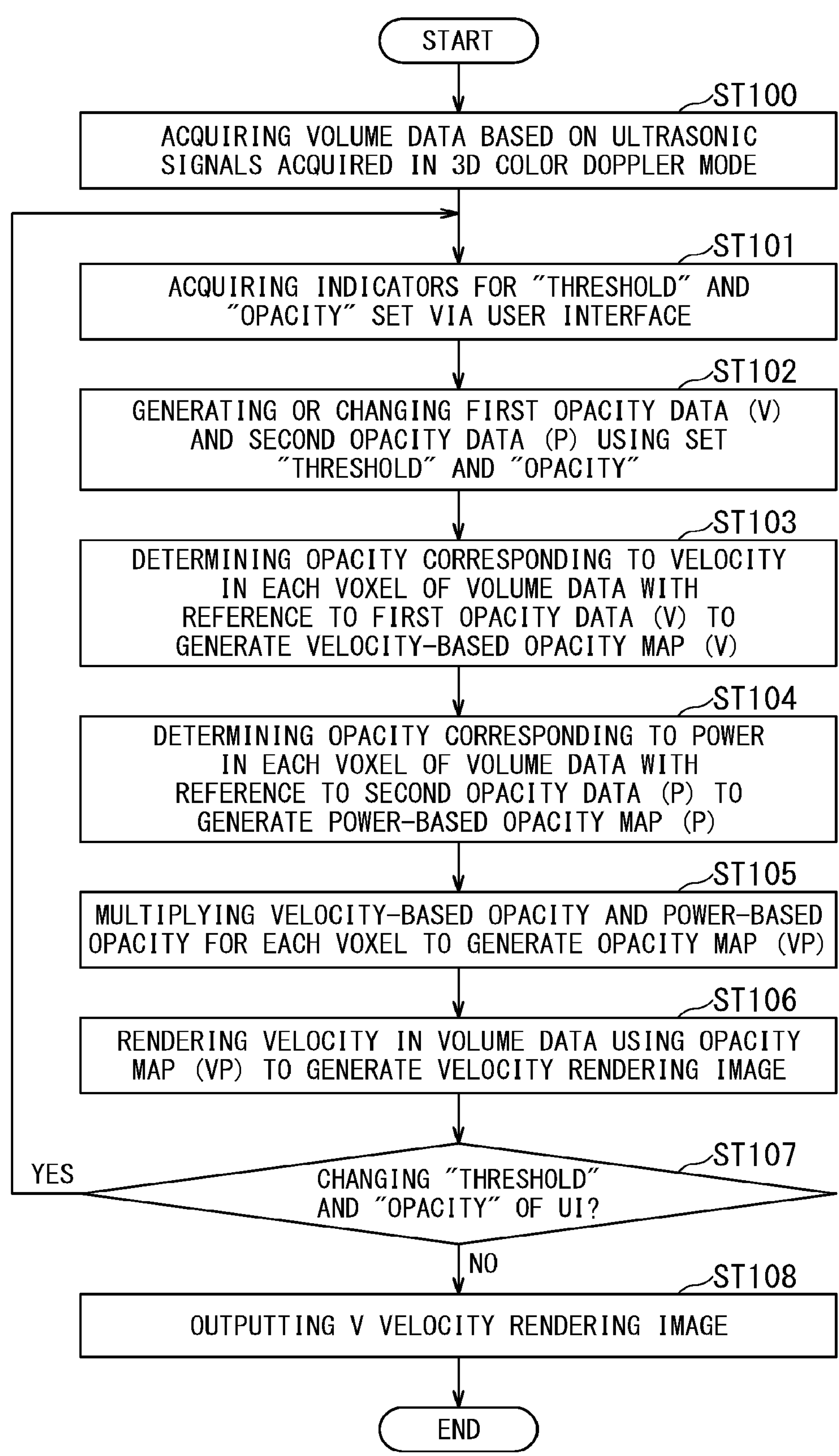
FIG. 3 is a flowchart showing an example of an operation of the ultrasonic image processing apparatus according to the first embodiment.

FIG. 3 is a flowchart showing an example of an operation of the ultrasonic image processing apparatus 20 according to the first embodiment. The ultrasonic image processing apparatus 20 renders volume data collected in 3D color doppler mode. The ultrasonic image processing apparatus 20 performs rendering processing of the volume data collected in 3D color doppler mode. The above functions realized by the processing circuitry 205 of the ultrasonic image processing apparatus 20 are described below in accordance with the flowchart in FIG. 3, with reference to FIGS. 4 through 10.

In step ST100 of FIG. 3, volume data based on ultrasonic signals collected in 3D color doppler mode is acquired. For example, but not limited to, volume data may be collected and generated by the ultrasonic diagnostic apparatus 1. For example, volume data collected by other ultrasonic diagnostic apparatuses may be acquired from an image server (not shown) via an electronic communication line such as LAN (Local Area Network) or the Internet, or via a storage medium such as USB memory or optical disk. It may also be obtained via a recording medium such as USB memory, optical disk, and the like.

Figure 4:
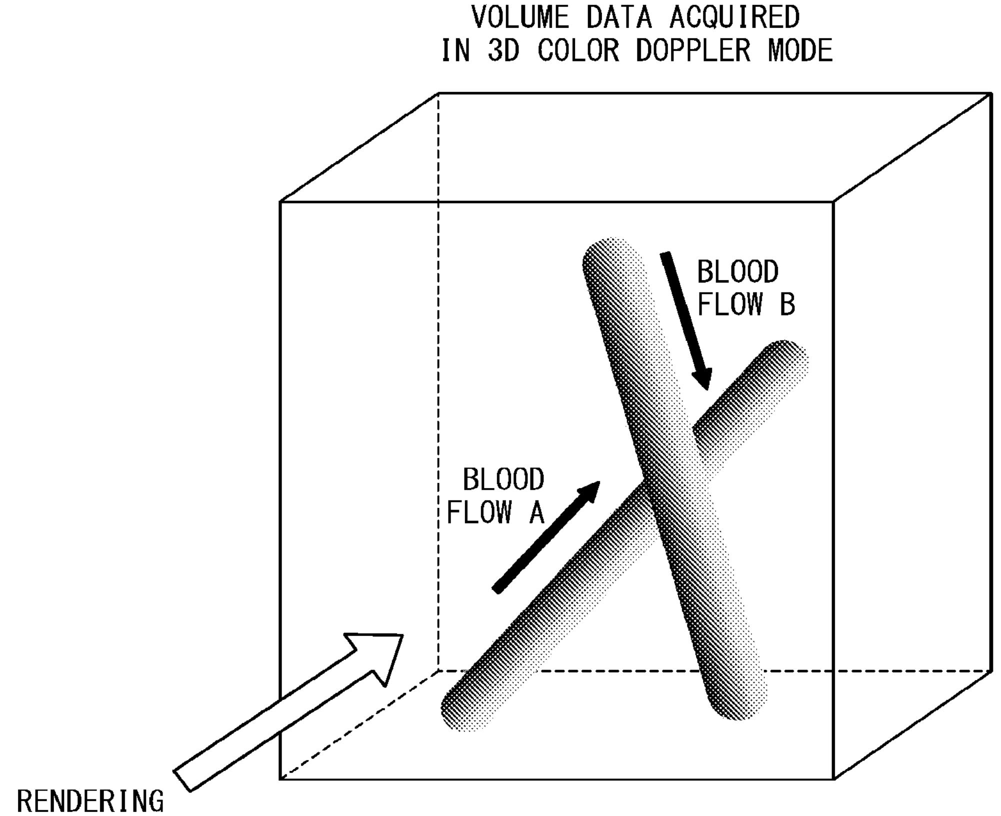
FIG. 4 is a schematic diagram showing an example of a volume data acquired in a 3D color doppler mode.

FIG. 4 is a schematic diagram showing an example of a volume data acquired in a 3D color doppler mode in step ST100. The volume data consists of a large number of voxels corresponding to a given resolution, each voxel holds data related to the blood flows of multiple blood vessels (e.g., blood flow A and blood flow B). Specifically, each voxel holds data on the average velocity, variance of velocity, and power of the blood flow. The volume data acquisition function F02 performs step ST100.

In the next step ST101, indexes related to "threshold" and "opacity" set via the user interface 202 are acquired.

Figure 5:
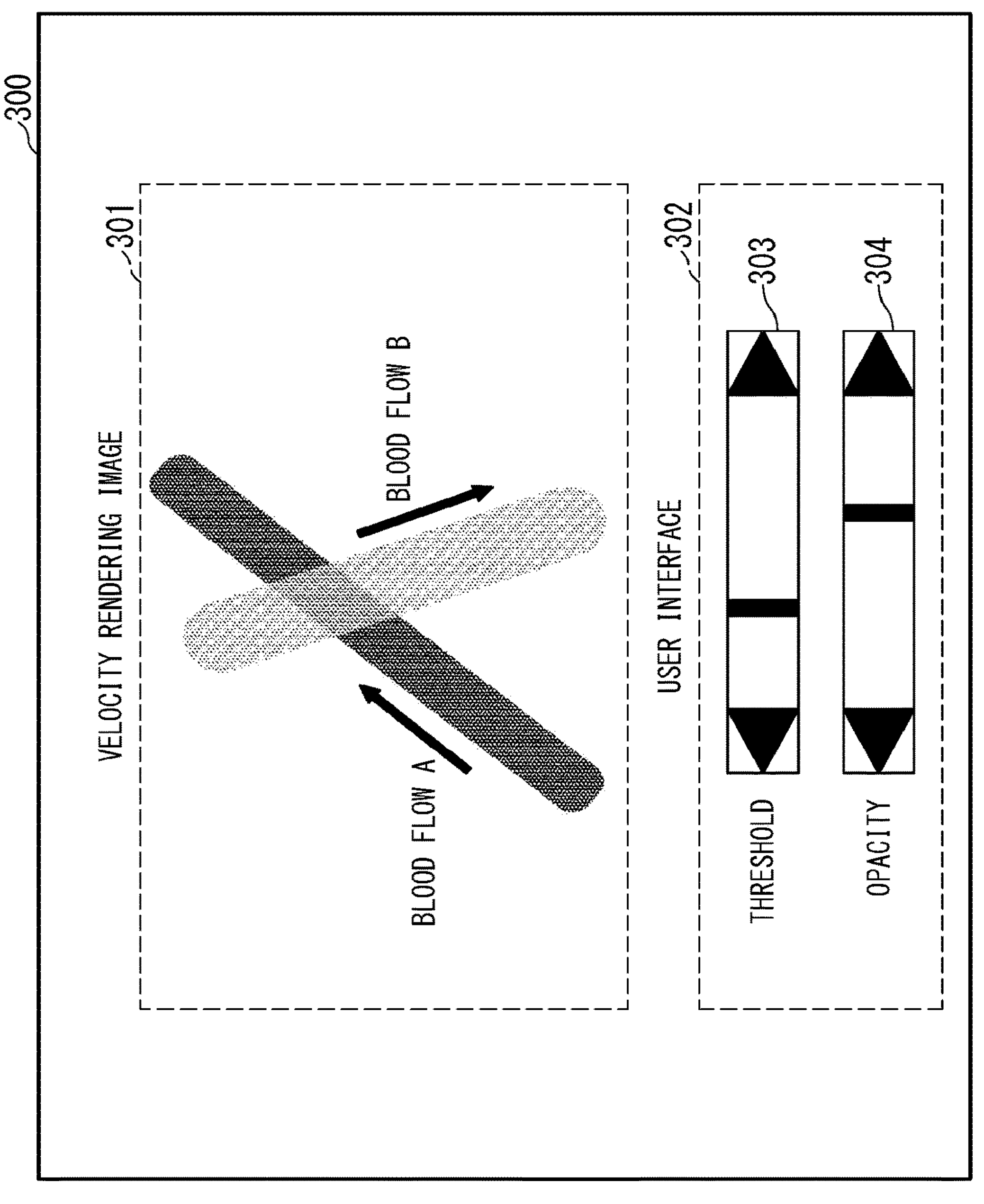
FIG. 5 is a diagram showing an example of a user interface display on a display screen and a velocity rendering image.

FIG. 5 is a diagram showing an example of a user interface display 302 and a velocity rendering image 301 shown on a screen 300 of the display 204. The velocity rendering image 301 is the image output in the last step ST108 of the flowchart.

The indexes for "threshold" and "opacity" are set according to the user who operates, via the input device 203 such as a mouse, the slide bar 303 for "threshold" settings and the slide bar 304 for "opacity" settings displayed on the user interface display 302, for example. In step ST101, the indexes for the "threshold" and "opacity" set in this way are obtained. The user interface setting value acquisition function F01 performs step ST101.

In step ST102, the first opacity data (V) and the second opacity data (P) are generated or changed using the set "threshold" and "opacity". The second opacity data (P) generation function F03 and the first opacity data (V) generation function F04 performs step ST102.

Figure 7:
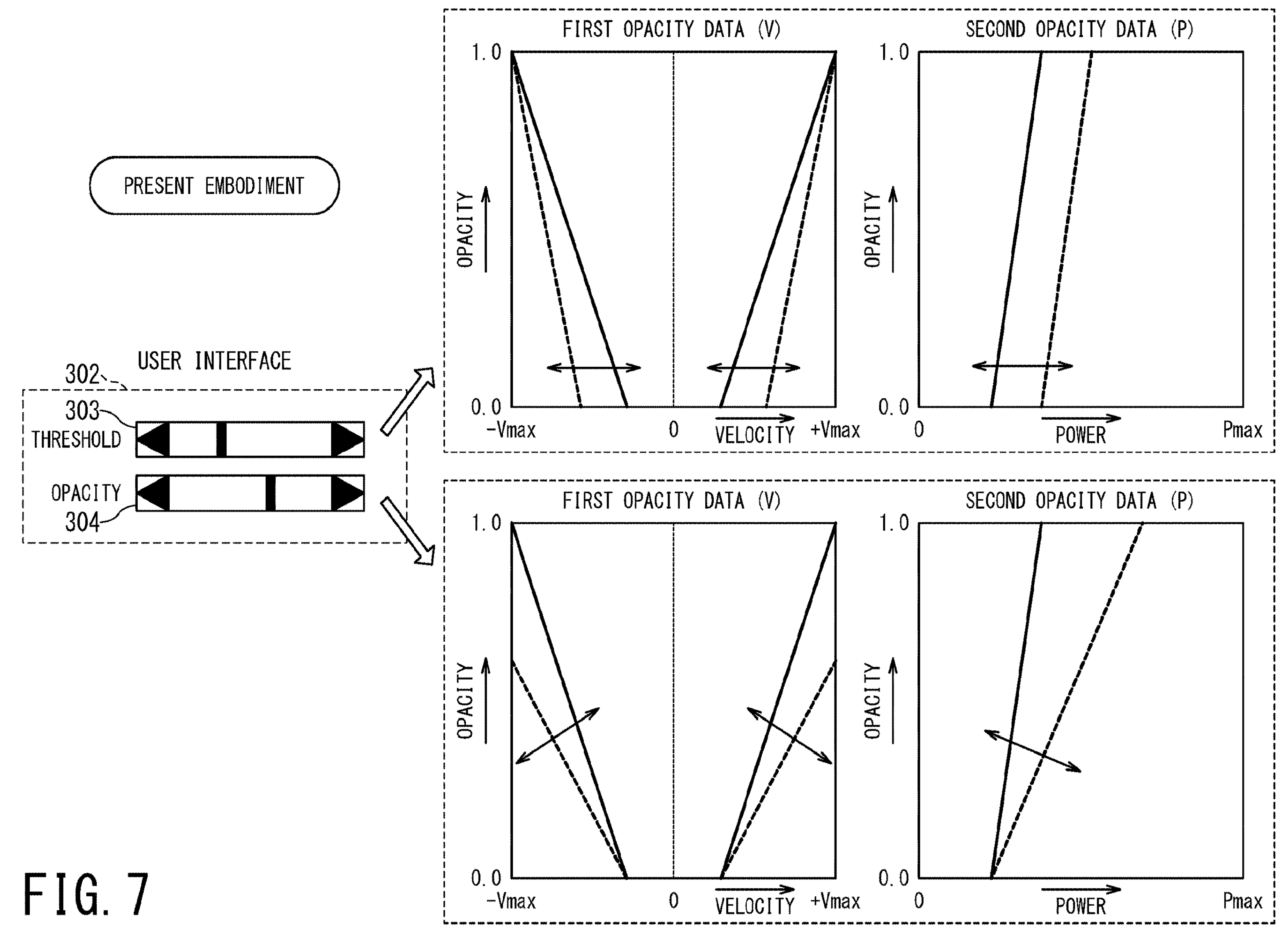
FIG. 7 is the first explanatory diagram showing an example of a process of generating and changing the opacity data by the ultrasonic image processing apparatus according to the first embodiment.
Figure 8:
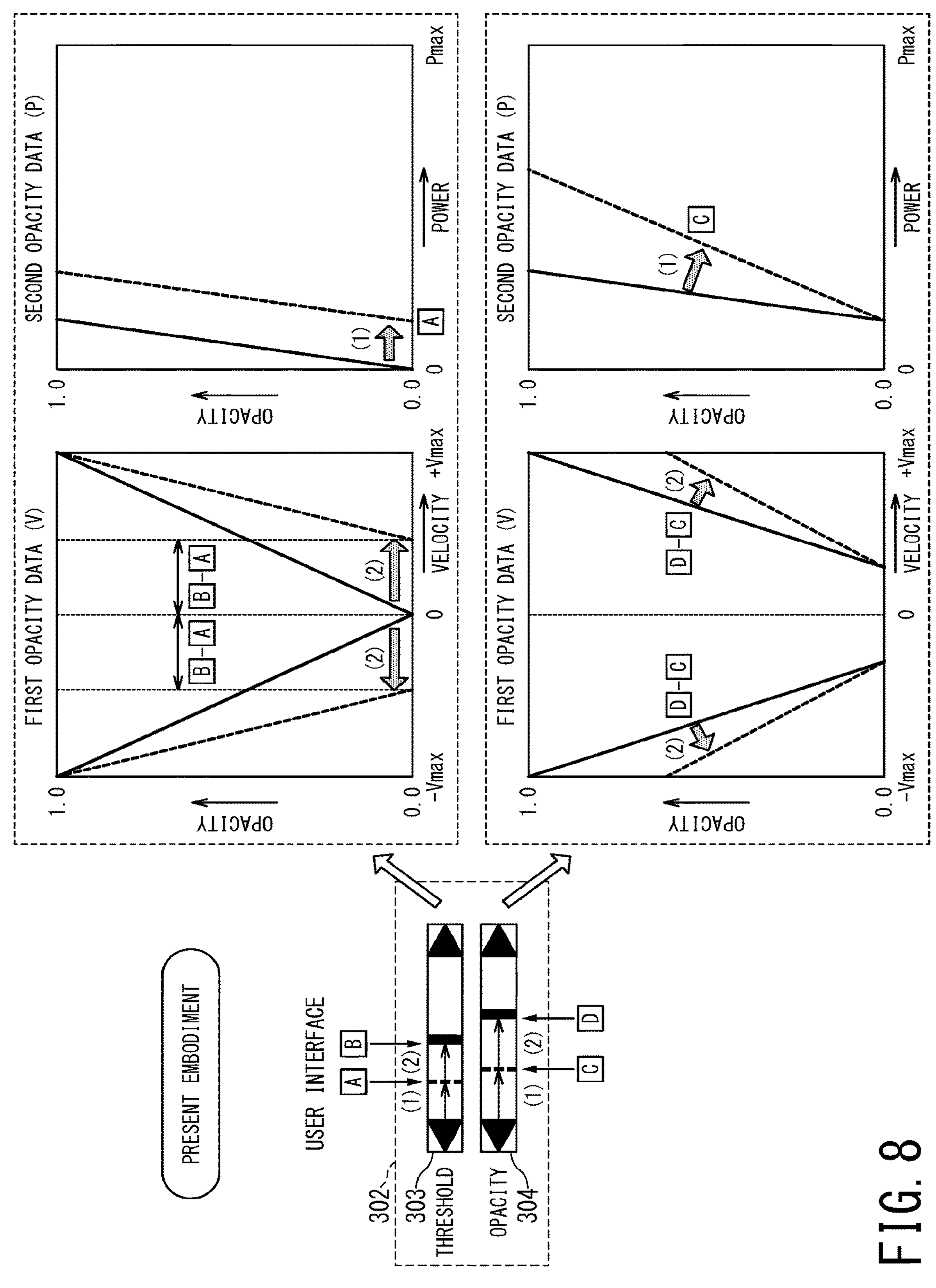
FIG. 8 is the second explanatory diagram showing an example of a process of generating and changing the opacity data by the ultrasonic image processing apparatus according to the first embodiment.

FIGS. 7 and 8 are the explanatory diagrams showing examples of a process of generating and changing the opacity data by the ultrasonic image processing apparatus 20 according to the first embodiment. The ultrasonic image processing apparatus 20 according to the first embodiment generates two opacity data, that is the first opacity data (V) and the second opacity data (P).

Figure 6:
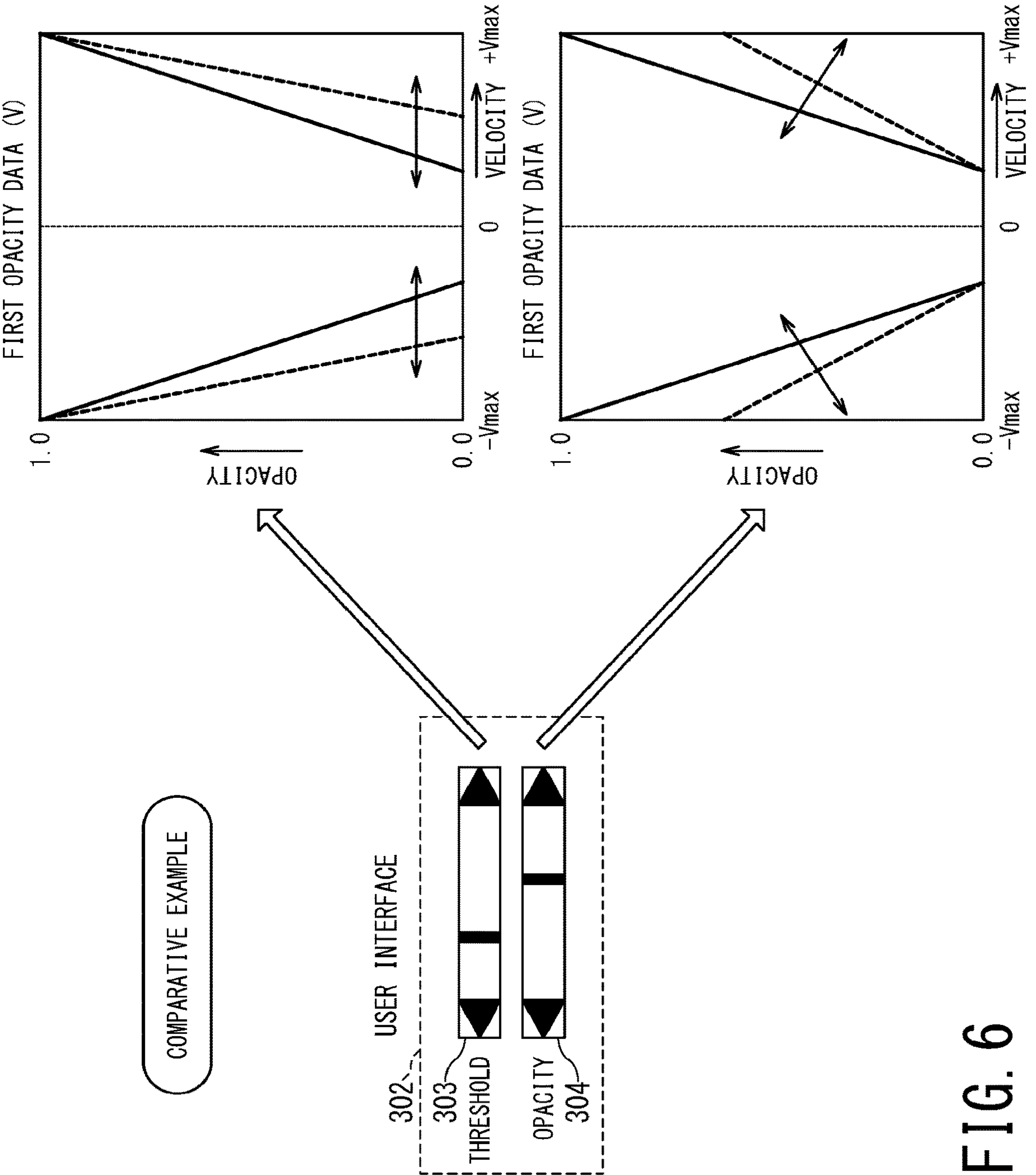
FIG. 6 is an explanatory diagram showing an example of a conventional process of generating and changing opacity data.

FIG. 6 is an explanatory diagram showing an example of the conventional process of generating and changing the opacity data as a comparative example to the processing of the embodiment. An example of opacity data is shown on the right side of FIG. 6. The opacity data is data that defines the relationship between fluid velocity and opacity, and is used when rendering volume data collected in the color Doppler mode. The velocity rendering image can be generated by setting the opacity that is related by the opacity data to the velocity values in each voxel of the volume data and rendering from a predetermined rendering direction (see FIG. 4).

The example of opacity data shown in FIG. 6 specifies the relationship between velocity and opacity, where the opacity changes linearly for velocities above a predetermined threshold value, while the opacity is zero, that is, the voxel in question is not displayed by making it completely transparent, for velocities below the predetermined threshold value.

In the conventional process of generating and changing opacity data, the threshold value of the opacity data is set or changed by the user setting or changing the "threshold value" slide bar 303 on the user interface display 302 shown on the left side of FIG. 6 (upper right side of FIG. 6). In addition, the slope of the line indicating the velocity versus opacity relationship of the opacity data was set or changed by the user setting or changing the "Opacity" slide bar 304 on the user interface display 302 (lower right side of FIG. 6).

However, this conventional method has the problem that the user does not always obtain the desired velocity rendering image because there is little freedom in setting or changing the opacity data. For example, when the "threshold value" was increased to make the boundary of the blood flow region in the velocity image clearer, the low velocity blood flow region, which was originally necessary, was lost or unwanted noise was drawn.

To solve these problems, the ultrasonic image processing apparatus 20 of the first embodiment generates two types of opacity data: first opacity data (V) and second opacity data (P).

Here, the first opacity data (V) is shown in the upper and lower center of FIG. 7 and is substantially the same as the opacity data used in the conventional example described above. The first opacity data (V) is data that defines the relationship between velocity and opacity, as described above. The relationship between velocity and opacity may be linear or nonlinear.

FIG. 7 is a diagram showing an example of the first opacity data (V). In FIG. 7, an example is shown in which the first opacity data (V) changes opacity linearly for velocities above a predetermined threshold value, while for velocities below a predetermined specified value, opacity is zero, that is, the voxel is not displayed by making it completely transparent.

The second opacity data (P) is shown in the upper and lower rows on the right side of FIG. 7 and defines the relationship between power and opacity. The relationship between power and opacity in the second opacity data (P) may also be linear or nonlinear.

In the example shown in FIG. 7, for example, the second opacity data (P) specifies the relationship between power and opacity, where opacity changes linearly for power above a predetermined threshold, while opacity is zero for power below a predetermined specified value, that is, the voxel is not displayed by making it completely transparent. In the first embodiment, the first opacity is defined by the first power.

In the first embodiment, two opacity data, i.e., the first opacity data (V) and the second opacity data (P), are used. As a result, four parameters can be adjusted: the threshold of velocity in the first opacity data (V); the slope of the line indicating the relationship between velocity and opacity; the threshold of power in the second opacity data (V); and the slope of the line indicating the relationship between power and opacity. Therefore, the degree of freedom in setting and changing opacity data is higher than that of the aforementioned conventional opacity data, and it is easier to obtain the Velocity rendering image desired by the user than in the past.

However, when the above four parameters are adjusted independently for setting and changing the first opacity data (V) and second opacity data (P), the burden on the user for adjusting the parameters will be large.

Therefore, the ultrasonic image processing apparatus 20 of the first embodiment uses two types of opacity data, the first opacity data (V) and the second opacity data (P), while the above four parameters of these two types of opacity data are adjusted independently. The four parameters can be adjusted in the same way as before, with two user interfaces: the "threshold" slide bar 303 for adjusting the "threshold value" and the "opacity" slide bar 304 for adjusting the "opacity". In the ultrasonic image processing apparatus 20 according to the first embodiment, as in the past, the "threshold" index that defines the lower limit of the velocity displayed in the velocity rendering image and the "opacity" index that defines the relationship between the velocity used for volume rendering and the opacity can be adjusted using two user interfaces. The user interface display 302 is configured such that the user can specify the "opacity" index that defines the relationship between the opacity and the velocity used for volume rendering. The first opacity data (V) and the second opacity data (P) described above are generated based on at least one of the "threshold" index and the "opacity" index specified via the user interface display 302.

FIG. 8 is a diagram showing an example of how to adjust the four parameters of the first opacity data (V) and the second opacity data (P) using the two slide bars 303 and 304.

In the example shown in FIG. 8, when the parameters of the first opacity data (V) and the second opacity data (P) are changed based on at least one of the "threshold" index and the "opacity" index, the second opacity data (P) is changed preferentially over the first opacity data (V).

More specifically, when the value of the "threshold" index set via the "threshold" slide bar 303 is below a predetermined value (e.g., when the "threshold" index is set in the range of "A" or less), the threshold in the second opacity data (P) is changed based on the set "threshold" index, as indicated by arrow (1) in the upper right-side of FIG. 8. The threshold value in the first opacity data (V) is not changed while the threshold value in the second opacity data (P) is changed (e.g., set to "A") based on the set "threshold" index.

Meanwhile, when the "threshold" index set via the "threshold" slide bar 303 is greater than the predetermined value (e.g., the "threshold" index is set to "B" greater than the predetermined value "A"), the threshold value in the first opacity data (V) is changed to the difference between the set "threshold" index and the predetermined value (e.g., "B" minus "A") as shown by arrow (2) in the upper middle of FIG. 8. and the predetermined value, while the threshold value in the second opacity data (P) remains unchanged (i.e., remains at "A", which has already been set).

Similarly, when the value of the "opacity" index set via the "opacity" slide bar 304 is less than a predetermined value (e.g., when it is set in the range of "C" or less), as indicated by arrow (1) in the lower right side of FIG. 8, the opacity slope in the second opacity data (P) is set (e.g., set to "C"), while the opacity slope in the first opacity data (V) remains unchanged.

Meanwhile, when the "opacity" index set via the "opacity" slide bar 304 is greater than the predetermined value (e.g., when it is set to "D" greater than the predetermined value "C"), as indicated by arrow (2) in the lower center of FIG. 8, the opacity slope in the first opacity data (V) will be changed to the set As shown by arrow (2) in the lower middle of FIG. 8, the opacity slope in the first opacity data (V) is changed based on the difference between the set “opacity” index and the predetermined value (for example, “D” minus “C”), while the opacity slope in the second opacity data (P) remains unchanged (remains at “C”, which has already been set).

Returning to FIG. 3, the process from step ST103 to step ST105 is to generate an opacity map (VP) using the first opacity data (V) and second opacity data (P) generated in step ST102. The process from step ST103 to step ST105 is performed by the capacity map (VP) generation function F05 in FIG. 2.

In step ST106, a velocity rendering image is generated by rendering the pixel values corresponding to the velocities in the volume data using the opacity map (VP) generated in step ST105. Step ST106 is processed by rendering function F06 in FIG. 2.

Figure 9:
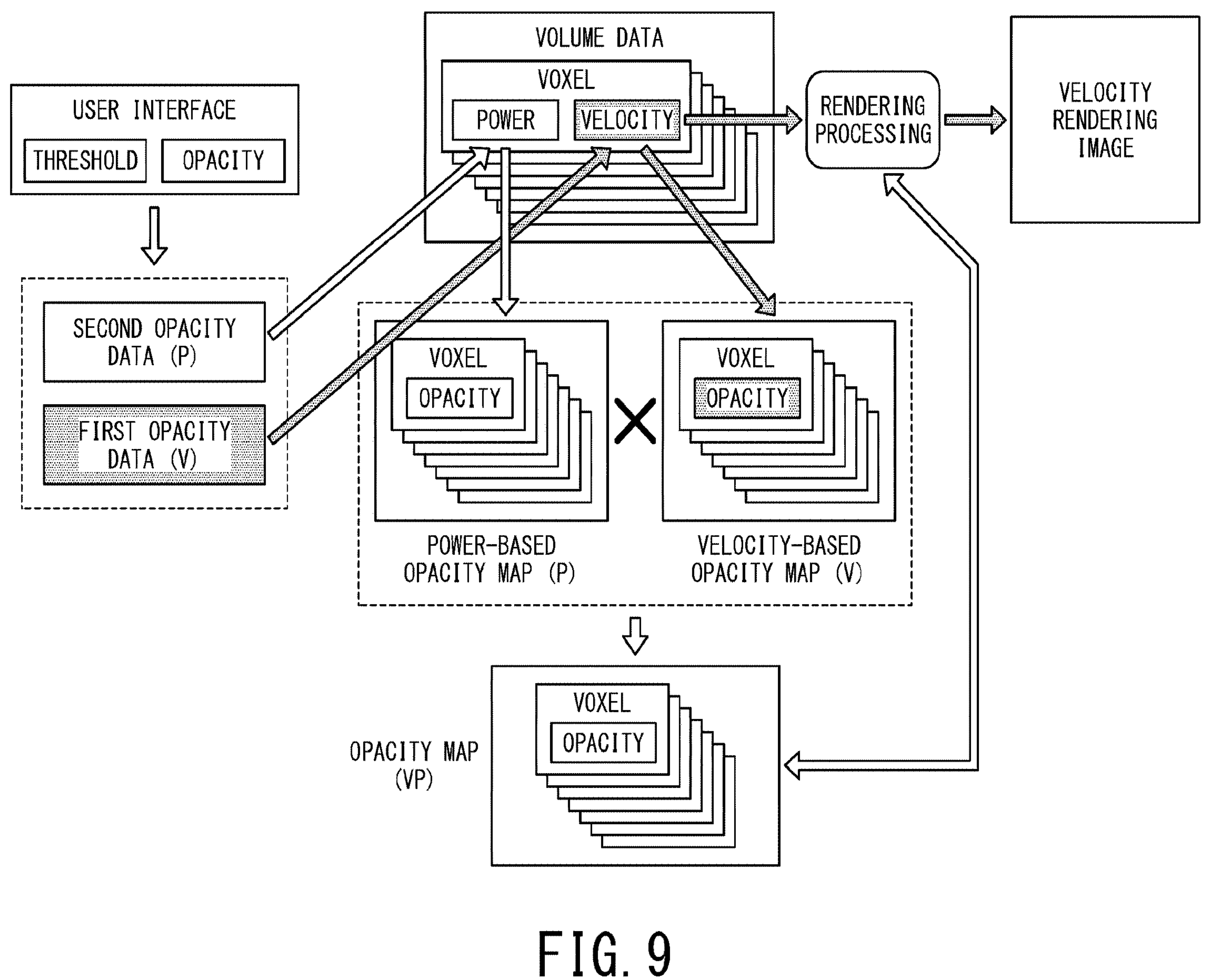
FIG. 9 is an explanatory diagram showing an example concept of a rendering process using a generation process of the opacity map in the first embodiment.

FIG. 9 is an diagram showing a process from step ST103 to step ST106. In step ST103, the opacity corresponding to the velocity contained in each voxel of the volume data is determined by referring to the first opacity data (V) to generate the velocity-based opacity map (V).

In the next step ST104, the opacity corresponding to the power contained in each voxel of the volume data is determined with reference to the second opacity data (P) to generate the power-based opacity map (P).

Then, in step ST105, the opacity map (VP) is generated by multiplying the velocity-based opacity generated in step ST103 and the power-based opacity generated in step ST104 for each voxel.

In step ST106, the opacity map (VP) is used to render the velocity contained in the volume data to generate a velocity rendering image.

The generated the velocity rendering image is displayed on the display 204 of the ultrasonic image processing apparatus 20, for example. If the user evaluates this velocity rendering image and determines that another adjustment is necessary, at least one of the “threshold” and “opacity” of the user interface display 302 will be changed (YES in step ST107), and the display returns to step ST101.

On the other hand, when the generated Velocity rendering image is the desired image and it is determined that another adjustment is necessary, the “threshold” and “opacity” of the user interface display 302 do not need to be adjusted (NO in step ST107) and proceed to step ST108.

In step ST108, the generated velocity rendering image is output to, for example, ultrasonic diagnostic apparatus 1 or a specified image server.

Figures 10A, 10B:
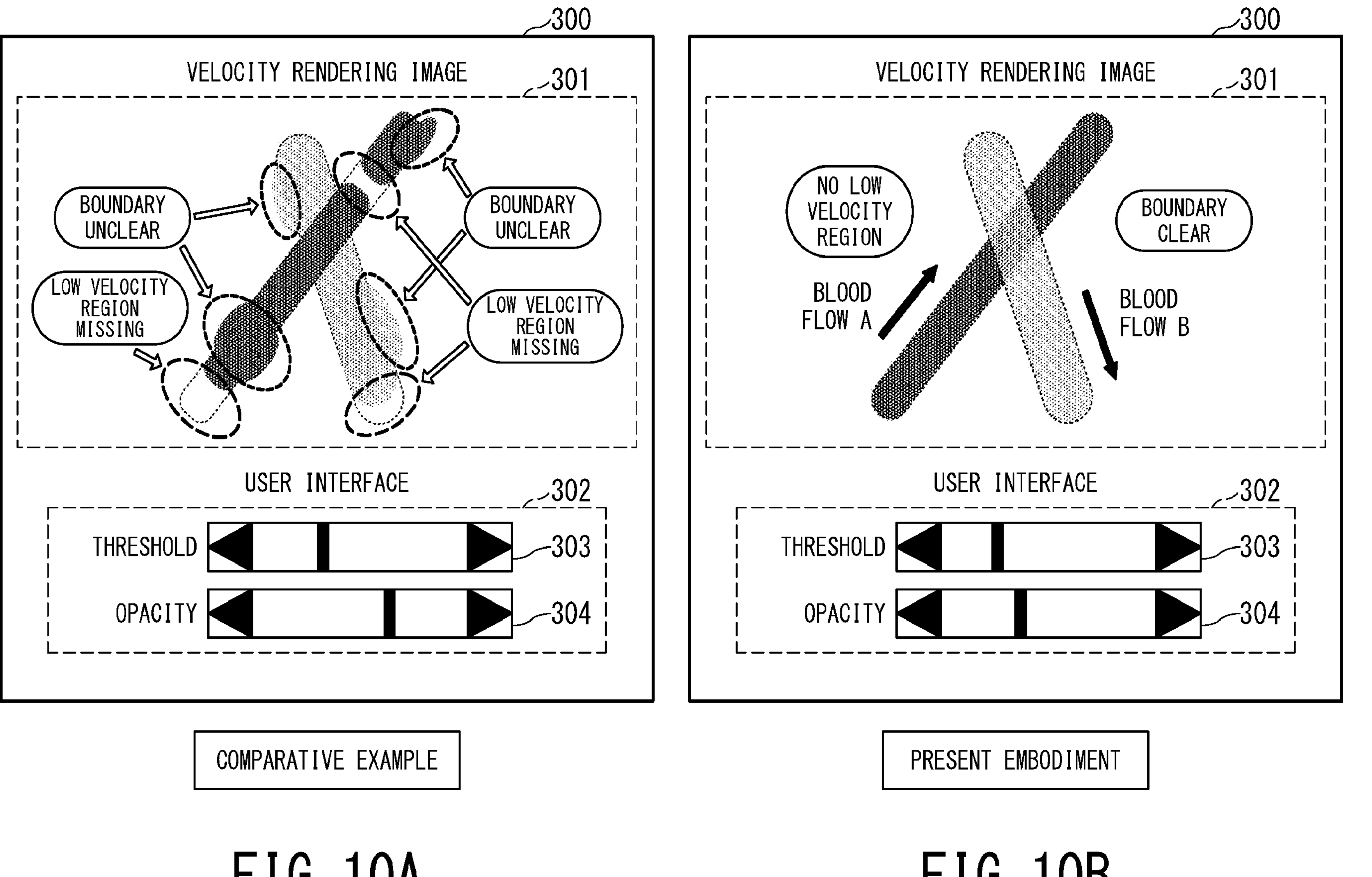
FIG. 10A is a comparative example showing the velocity rendering image generated by the conventional rendering process.
FIG. 10B is an explanatory diagram showing an example concept of an effect of the ultrasonic image processing apparatus according to the first embodiment.

FIGS. 10A and 10B are explanatory diagrams showing example concepts of the effect of the ultrasonic image processing apparatus 20 according to the first embodiment. FIG. 10A schematically shows the velocity rendering image generated by the conventional rendering process as a comparative example. As mentioned above, conventionally, the opacity data used in the rendering process is a single opacity data that defines the relationship between velocity and opacity, so there was little freedom in setting and changing the opacity data. Therefore, as shown in the comparative example Velocity rendering image in FIG. 10A, the low velocity blood flow region may be missing in part of the blood flow region, or the boundary of the region may be unclear. In addition, unnecessary noise areas that do not exist in the Velocity rendering image are sometimes depicted in the Velocity rendering image.

On the other hand, in the ultrasonic image processing apparatus 20 according to the first embodiment, the opacity map (VP) used in the rendering process is generated by using the velocity-based opacity map (V) generated from the first opacity data (V) and the power-based opacity map (P) generated from the second opacity data (P). Therefore, the user has a high degree of freedom to adjust the opacity map (VP) and can easily generate the Velocity rendering image desired by the user. For example, as schematically illustrated in FIG. 10B, it is possible to generate the velocity rendering image with no missing low velocity regions of blood flow and a blood flow region with clearly delineated boundaries.

As described above, according to the ultrasonic image processing apparatus 20 of the first embodiment, the velocity rendering image desired by the user can be generated from the volume data acquired by the ultrasonic diagnostic apparatus 1 in the 3D color doppler mode without imposing any operational burden on the user.

Second Embodiment

Figure 11:
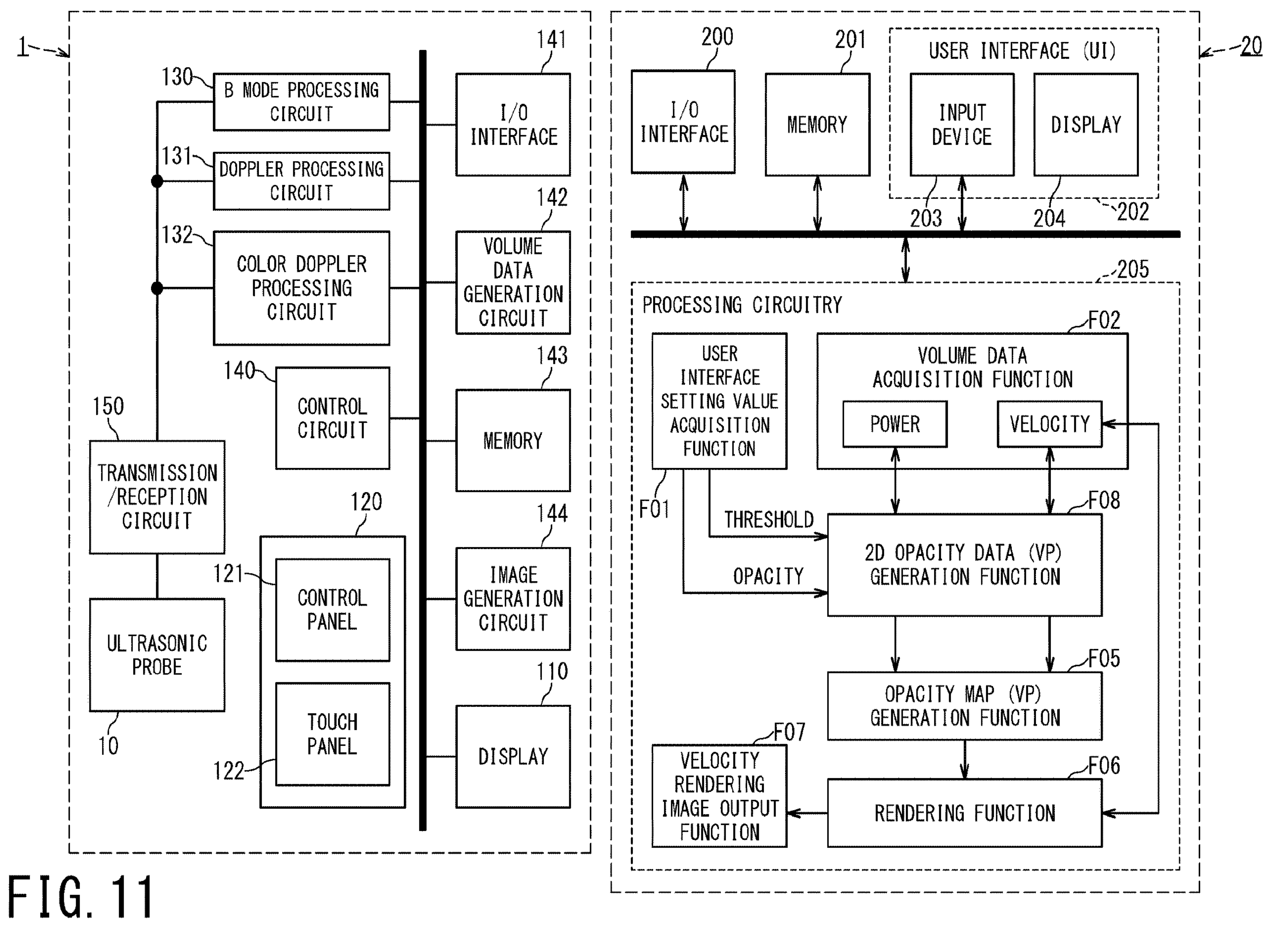
FIG. 11 is a block diagram showing an example of the ultrasonic diagnostic apparatus and the ultrasonic image processing apparatus according to the second embodiment.

FIG. 11 is a block diagram showing an example of the ultrasonic image processing apparatus 20 and the ultrasonic diagnostic apparatus 1 of the second embodiment. The difference from the first embodiment is that the processing circuitry of the ultrasonic image processing apparatus 20 of the second embodiment has a 2D opacity data (VP) generation function F08 instead of the second opacity data (P) generation function F03 and the first opacity data (V) generation function F04.

In the second embodiment of the ultrasonic image processing apparatus 20, the 2D opacity data (VP) generation function F08 generates 2D opacity data (VP) in which the relationship between the velocity and power and the opacity is defined. This 2D opacity data (VP) is used to generate the opacity map (VP).

Figure 12:
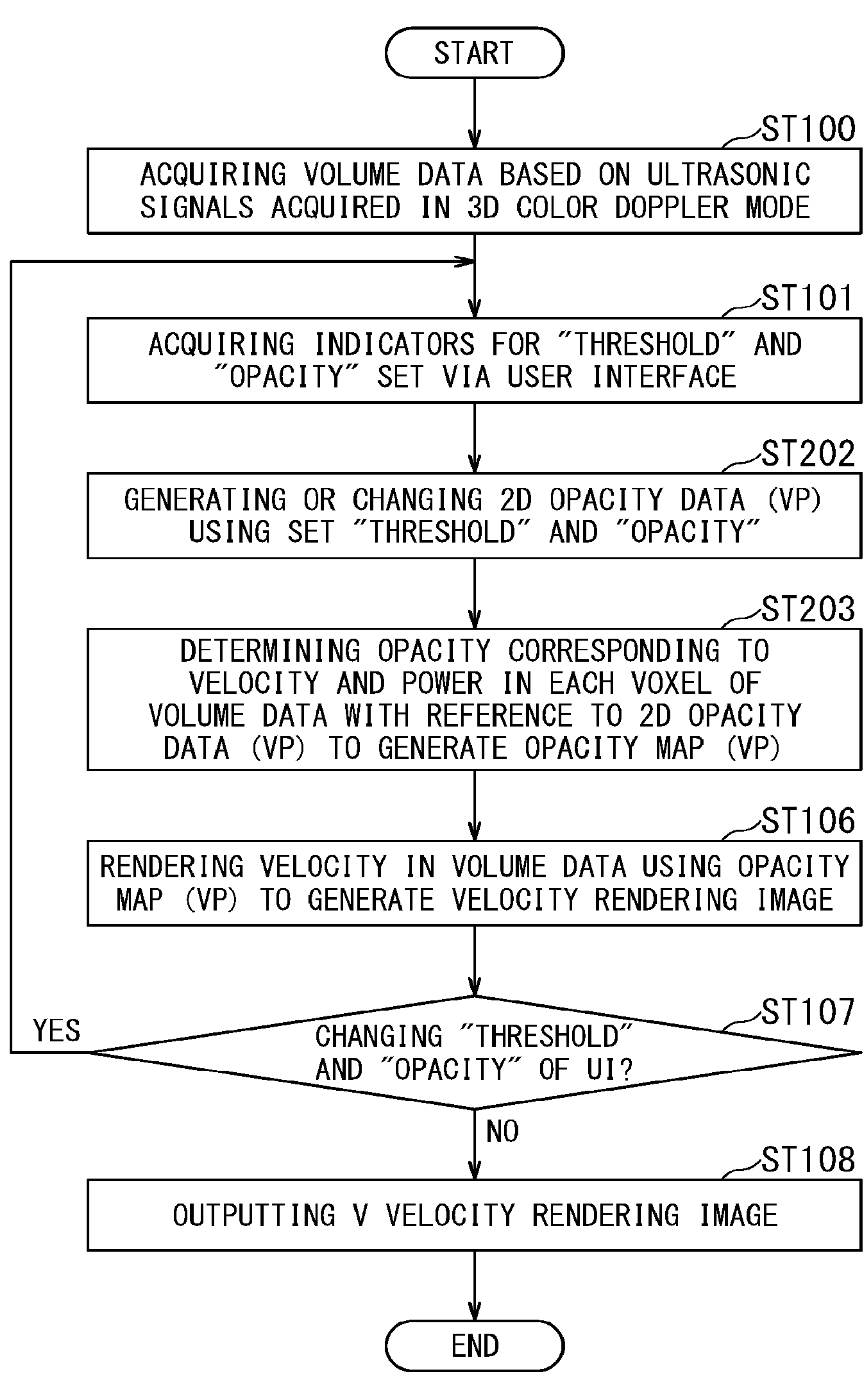
FIG. 12 is a flowchart showing an example of the operation of the ultrasonic image processing apparatus according to the second embodiment.

FIG. 12 is a flowchart showing an example of the operation of the ultrasonic image processing apparatus 20 according to the second embodiment. The difference from the flowchart of the first embodiment (shown in FIG. 3) is that the process according to the second embodiment shown in FIG. 12 has steps ST202 and ST203 instead of steps ST102 through ST105. For the same process as the first embodiment, the explanation is omitted.

Figure 13:
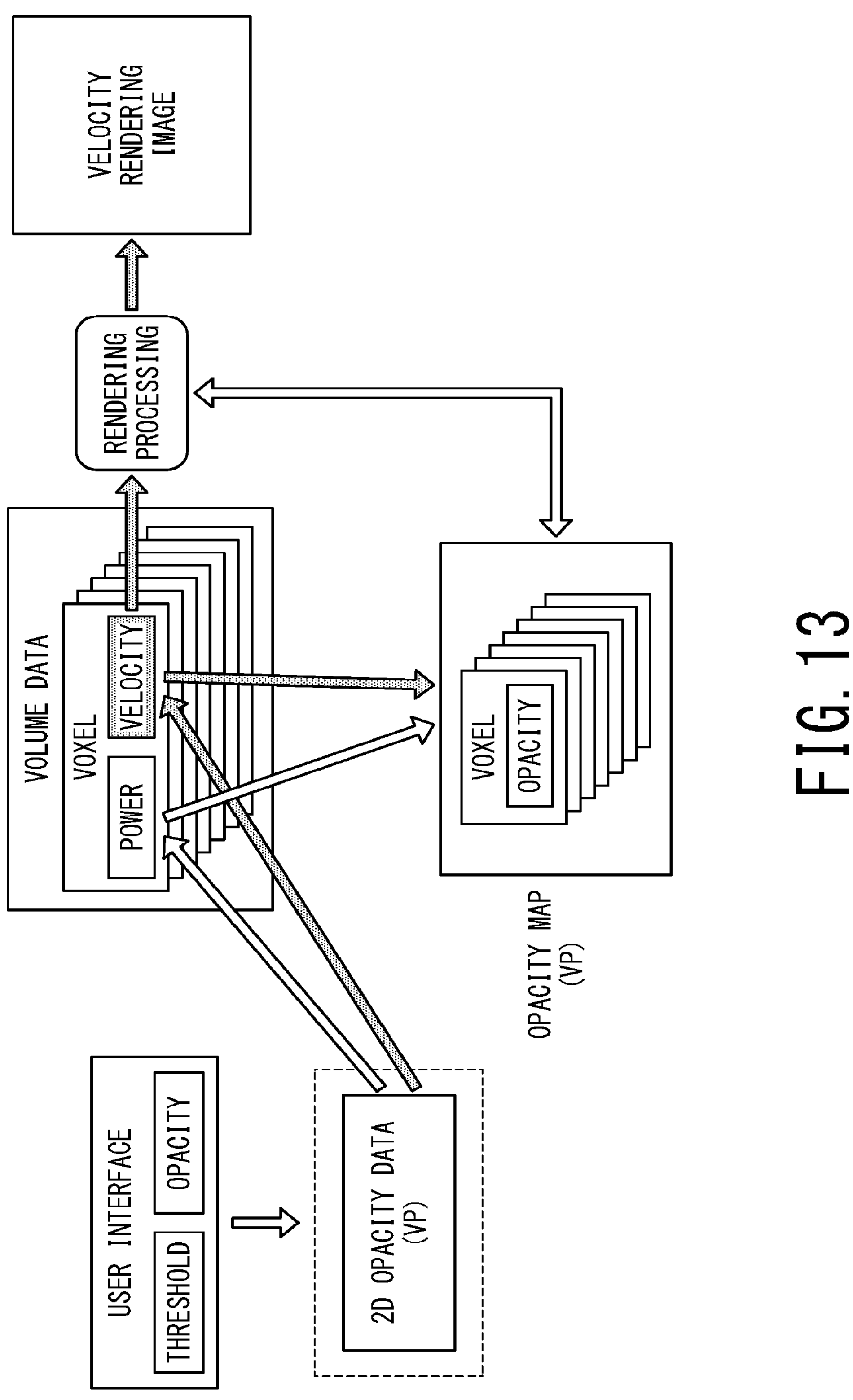
FIG. 13 is an explanatory diagram showing an example concept of a rendering process using the opacity map generation process in the second embodiment.

FIG. 13 is an explanatory diagram showing an example concept of the processing from step ST100 to step ST106, including the processing of step ST202 and step ST203.

In step ST202, 2D opacity data (VP) is generated based on the “threshold” and “opacity” set via the user interface display 302. 2D opacity data (VP) is a data set in which the relationship between velocity and power and opacity is specified. For example, 2D opacity data (VP) is a data set that has opacity values to be specified for coordinates (“velocity” and “power”) in a two-dimensional space with “velocity” on the X axis and “power” on the Y axis.

The second form of ultrasonic image processing apparatus 20 also has a “threshold” index that defines the lower limit of the velocity displayed in the velocity rendering image, and an “opacity” index that defines the relationship between the velocity and opacity used for volume rendering. The user interface display 302 is configured such that the user can specify the “opacity” index. The 2D opacity data (VP) described above is generated based on at least one of the “threshold” index and the “opacity” index specified via the user interface display 302.

When the 2D opacity data (VP) is changed based on at least one of the specified “threshold” index and “opacity”

index, the data corresponding to power is changed preferentially over the data corresponding to velocity in the 2D opacity data (VP).

In the next step ST203, by referring to 2D opacity data (VP), the opacity corresponding to the value of velocity and the value of power in each voxel of the volume data is determined for each voxel, and the opacity map (VP) is generated using the determined opacity for each voxel.

In step ST106, the opacity map (VP) generated as described above is used for rendering the velocity values (i.e., voxel values with velocity values) contained in the volume data to generate the velocity rendering image.

OTHER EMBODIMENTS

In each of the embodiments described above, the ultrasonic diagnostic apparatus 1 and the ultrasonic image processing apparatus 20 have been described as separate devices independent of each other, but are not limited thereto. The ultrasonic diagnostic apparatus 1 may be configured to have the configuration and functions of the ultrasonic image processing apparatus 20 described above.

As explained above, the ultrasonic image processing apparatus 20 and the ultrasonic diagnostic apparatus 1 of the present embodiments can generate the user's desired velocity rendering image from volume data acquired by the 3D color doppler mode of the ultrasonic diagnostic apparatus 1 without imposing any operational burden on the user.

The processing circuitry in the above-described embodiments is an example of the processing circuitry described in the claims. In addition, the term "processor" used in the explanation in the above-described embodiments, for instance, refers to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing the corresponding program. When a plurality of processors are provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic image processing apparatus, comprising:
processing circuitry configured to:
acquire volume data based on ultrasonic signals collected by 3D color doppler mode, wherein each voxel value of the volume data includes at least a value of a velocity of a fluid and a value of a power representing an intensity of echo signals of the fluid;
generate a velocity rendering image by volume rendering the volume data using an opacity map in which a relationship between an opacity of the voxel and both the velocity and the power is defined,
wherein the processing circuitry is further configured to:
generate first opacity data that defines the relationship between the velocity and the opacity, and second opacity data that defines the relationship between the power and the opacity; and
generate the opacity map using the first opacity data and the second opacity data.

2. The ultrasonic image processing apparatus according to claim 1, wherein the processing circuitry is further configured to;
generate a velocity-based opacity map by determining, for each voxel, the opacity corresponding to the value of the velocity included in each voxel of the volume data with reference to the first opacity data,
generate a power-based opacity map by determining, for each voxel, the opacity corresponding to the value of the power contained in each voxel of the volume data with reference to the second opacity data, and
generate the opacity map by multiplying the velocity-based opacity map and the power-based opacity map for each voxel.

3. The ultrasonic image processing apparatus according to claim 1, further comprising a user interface configured to allow a user to specify a threshold index that defines a lower limit of the velocity to be displayed in the velocity rendering image and an opacity index that defines the relationship between the velocity and the opacity used for the volume rendering,
wherein the processing circuitry is further configured to generate the first opacity data and the second opacity data based on at least one of the threshold index and the opacity index specified via the user interface.

4. The ultrasonic image processing apparatus according to claim 3, wherein, when changing the first opacity data and the second opacity data based on the at least one of the threshold index and the opacity index, the processing circuitry is further configured to change the second opacity data preferentially over the first opacity data.

5. The ultrasonic image processing apparatus according to claim 3, wherein the processing circuitry is further configured to:
when the threshold index set via the user interface is a predetermined value or less, change the threshold value in the second opacity data based on the set threshold index, while leaving the threshold value in the first opacity data unchanged; and
when the threshold index set via the user interface is greater than the predetermined value, change the threshold in the first opacity data based on the difference between the set threshold index and the predetermined value, while leaving the threshold value in the second opacity data unchanged.

6. The ultrasonic image processing apparatus according to claim 3, wherein the processing circuitry is further configured to:

when the opacity index set via the user interface is a predetermined value or less, change the opacity in the second opacity data based on the set opacity index, while leaving the opacity in the first opacity data unchanged; and when the opacity index set via the user interface is greater than the predetermined value, change the opacity in the first opacity data based on the difference between the set opacity index and the predetermined value, while leaving the opacity in the second opacity data unchanged.

7. An ultrasonic image processing apparatus, comprising:

processing circuitry configured to:

acquire volume data based on ultrasonic signals collected by 3D color doppler mode, wherein each voxel value of the volume data includes at least a value of a velocity of a fluid and a value of a power representing an intensity of echo signals of the fluid;

generate a velocity rendering image by volume rendering the volume data using an opacity map in which a relationship between an opacity of the voxel and both the velocity and the power is defined, wherein the processing circuitry is further configured to:

generate two-dimensional opacity data in which the relationship between the opacity and both the velocity and the power is defined; and generate the opacity map using the two-dimensional opacity data.

8. The ultrasonic image processing apparatus according to claim 7, wherein the processing circuitry is further configured to:

determine, for each voxel, the opacity corresponding to the value of the velocity and the value of the power included in each voxel of the volume data by referring to the two-dimensional opacity data; and generate the opacity map using the determined opacity for each voxel.

9. The ultrasonic image processing apparatus according to claim 7, further comprising a user interface configured to allow a user to specify a threshold index that defines a lower limit of the velocity to be displayed in the velocity rendering image and an opacity index that defines the relationship between the velocity and the opacity used for the volume rendering, wherein the processing circuitry is further configured to generate the two-dimensional opacity data based on at least one of the threshold index and the opacity index specified via the user interface.

10. The ultrasonic image processing apparatus according to claim 9, wherein, when changing the two-dimensional opacity data based on the at least one of the threshold index and the opacity index, the processing circuitry is further configured to change the second opacity data preferentially over the first opacity data.

11. An ultrasonic diagnostic apparatus, comprising the ultrasonic image processing apparatus according to claim 1.

12. An ultrasonic image processing method, comprising:

acquiring volume data based on ultrasonic signals collected by 3D color doppler mode, wherein each voxel value of the volume data includes at least a value of a velocity of a fluid and a value of a power representing an intensity of echo signals of the fluid;

generating a velocity rendering image by volume rendering the volume data using an opacity map in which a relationship between the opacity of the voxel and both the velocity and the power is defined, wherein the method further comprises generating first opacity data that defines the relationship between the velocity and the opacity, and second opacity data that defines the relationship between the power and the opacity; and generating the opacity map using the first opacity data and the second opacity data.

13. An ultrasonic image processing method, comprising:

acquiring volume data based on ultrasonic signals collected by 3D color doppler mode, wherein each voxel value of the volume data includes at least a value of velocity of a fluid and a value of a power representing an intensity of echo signals of the fluid;

generating a velocity rendering image by volume rendering the volume data using an opacity map in which a relationship between the opacity of the voxel and both the velocity and the power is defined;

generate two-dimensional opacity data in which the relationship between the opacity and both the velocity and the power is defined; and generate the opacity map using the two-dimensional opacity data.

* * * * *